United States Patent [19]

Tso et al.

[11] Patent Number: 5,210,320

[45] Date of Patent: May 11, 1993

[54] PREPARATION OF 2,5-DIMETHYLHEXANE-2,5-DIHYDROPEROXIDE AND DERIVATIVES THEREOF

[75] Inventors: Chung C. Tso; Joe W. Ryker, both of Bartlesville, Okla.

[73] Assignee: Phillips Petroleum Company, Bartlesville, Okla.

[21] Appl. No.: 930,588

[22] Filed: Aug. 17, 1992

[51] Int. Cl.$^5$ ............................................. C07C 409/22
[52] U.S. Cl. ................................... 568/561; 568/562; 568/578
[58] Field of Search ..................... 568/561, 562, 578

[56] References Cited

U.S. PATENT DOCUMENTS

| | | | |
|---|---|---|---|
| 3,086,966 | 4/1963 | Mageli et al. | 568/561 |
| 3,117,166 | 1/1964 | Harrison et al. | 568/561 |
| 3,135,805 | 6/1964 | Gilmont | 568/561 |
| 3,214,422 | 10/1965 | Mageli et al. | 568/561 |

FOREIGN PATENT DOCUMENTS 0023661 2/1983 Japan ................................ 568/561

Primary Examiner—Werren B. Lone
Attorney, Agent, or Firm—Lucas K. Shay

[57] ABSTRACT

A one-step process for preparing 2,5-dimethylhexane-2,5-dihydroperoxide and its alkyl derivatives comprises: (1) adding sulfuric acid to a 60–70% hydrogen peroxide solution to form a first reaction mixture where the first mixture is controlled at a temperature in the range of from about −10° C. to about 10° C.; (2) adding 2,5-dimethyl-2,5-dihydroxy hexane to the mixture held at a temperature in the range of from about −10° C. to about 10° C. or lower to form a second reaction mixture and maintaining the second mixture at a temperature in the range of from about 20° C. to about 50° C. for about 5 minutes to about 5 hours to form a slurry containing the solid product of 2,5-dimethylhexane-2,5-dihydroperoxide, unreacted reactants and impurities; (3) lowering the temperature of the slurry to the range of from about −10° C. to about 10° C.; (4) removing unreacted reactants and impurities from the solid product and optionally, washing the solid product; and (5) adding sulfated alkyl alcohol, which is prepared by adding the alkyl alcohol to sulfuric acid, to the solid product to form a third reaction mixture and maintaining the third mixture at about 30° C. to about 60° C. for about 1 to about 5 hours to prepare the alkyl derivatives.

10 Claims, No Drawings

PREPARATION OF 2,5-DIMETHYLHEXANE-2,5-DIHYDROPEROXIDE AND DERIVATIVES THEREOF

FIELD OF THE INVENTION

The present invention relates to the preparation of 2,5-dimethylhexane-2,5-hydroperoxide and its derivatives.

BACKGROUND OF THE INVENTION

The peroxide 2,5-dimethylhexane-2,5-dihydroperoxide and its derivatives are a class of important industrial peroxide compounds. They are useful as initiators in free radical polymerization process. They are also useful peroxy compounds in visbreaking of polyolefins.

These peroxy compounds have been prepared by, for example, first reacting 2,5-dimethyl-2,5-dihydroxyhexane with 50% hydrogen peroxide in sulfuric acid to synthesize 2,5-dimethylhexane-2,5-dihydroperoxide followed by washing. This 2,5-dimethylhexane-2,5-dihydroperoxide is further reacted with disfunctional chloride, acyl chlorides, haloformate and related material, benzaledehyde, an aliphatic alcohol in an inorganic acid, and the like to prepare its diperoxy derivatives. See U.S. Pat. No. 3,117,166 (Jan. 7, 1964).

The shortcomings of the above-described two stage process are: (1) the 2,5-dimethylhexane-2,5-dihydroperoxide is isolated as solid which is acid- and heat-labile, specially when it is dry; (2) considerable time is consumed in the isolation step; and (3) the diperoxy derivatives, for example, 2,5-dimethyl-2,5-di(butylproxy) hexane, thus prepared are found to produce color and odor in visbreaking operations. First, the 2,5-dimethylhexane-2,5-dihydroperoxide, when treated with an acid to prepare its derivatives, is believed to undergo an acid-catalyzed heterolysis to products comprising acetone, ethylene glycol and other derivatives. Secondly, in order to isolate the 2,5-dimethylhexane-2,5-dihydroperoxide, a repeated washing step is required. Finally, the referenced process also produces, in addition to the desired conversion, 5- and 6-membered ring compounds, 2,5-2,2,5,5-tetramethyldihydrofuran and 3,3,6,6-tetramethyl-1,2-dioxacyclohexane, respectively. These cyclic compounds are formed because of the thermodynamically favored internal cyclization of 2,5-dimethyl-2,5-dihydroxy hexane.

It would therefore be a significant contribution to the art if a simplified process, which substantially improves the overall yield of the peroxy compounds and reduces the cyclic compounds contributing to undesired color and odor, is developed.

SUMMARY OF THE INVENTION

Accordingly, an object of the present invention is to provide a simplified one step process to prepare derivatives of 2,5-dimethylhexane-2,5-dihydroperoxide. Another object of the present invention is to provide a process for improving the yield of 2,5-dimethylhexane-2,5-dihydroperoxide and its derivatives. A further object of the present invention is to substantially reduce the cyclic compounds and, consequently, odor and color when used in visbreaking of polyolefins. Other objects, advantages, and futures will become apparent as the invention is more fully disclosed.

According to the present invention a one-step process for preparing 2,5-dimethylhexane-2,5-dihydroperoxide and its alkyl derivatives comprises: (1) adding sulfuric acid to an at least 60% hydrogen peroxide solution to form a first reaction mixture where the first mixture is controlled at a temperature in the range of from about $-10°$ C. to about $10°$ C.; (2) adding 2,5-dimethyl-2,5-dihydroxy hexane to the mixture held at a temperature in the range of from about $-10°$ C. to about $10°$ C. or lower to form a second reaction mixture and maintaining the second reaction mixture at a temperature in the range of from about $20°$ C. to about $50°$ C. for about 5 minutes to about 5 hours to form a slurry containing the solid product of 2,5-dimethylhexane-2,5-dihydroperoxide, unreacted reactants and impurities; (3) lowering the temperature of the slurry to the range of from about $-10°$ C. to about $10°$ C.; (4) removing unreacted reactants and impurities from the solid product and optionally, washing the solid product; and (5) adding sulfated alkyl alcohol, which is prepared by adding the alkyl alcohol to sulfuric acid, to the solid product to form a third reaction mixture and maintaining the third mixture at about $30°$ C. to about $60°$ C. for about 1 to about 5 hours to prepare the alkyl derivatives.

DETAILED DESCRIPTION OF THE INVENTION

The alkyl derivatives of 2,5-dimethylhexane-2,5-dihydroperoxide of the present invention has the formula of $CH_3(CH_3)C(O_2R)CH_2$—$CH_2$-$C(O_2R)(CH_3)CH_3$ where R is an alkyl group having 1 to about 10 carbon atoms. One and only one of the Rs can be a hydrogen. The alkyl group can be linear, cyclic, or branched.

Preparation of 2,5-dimethylhexane-2,5-dihydroperoxide and its alkyl derivatives can be carried out in any reaction vessels that are equipped with temperature control mechanisms. In the first step of the preparation, sulfuric acid is added to an at least 60% hydrogen peroxide to form a sulfuric acid-hydrogen peroxide mixture. The molar ration of hydrogen peroxide to sulfuric acid is in the range of from about 0.5 to about 10, preferably from about 1.0 to about 5, and most preferably from 1.2 to 2.5. The mixture is controlled at a temperature of about $10°$ C. or lower. The preparation of the mixture can be carried out under any pressure in the range of from about 0.1 atmosphere to about 10 atmospheres, preferably at about 1 atmosphere.

In the second step, 2,5-dimethyl-2,5-dihydroxy hexane is added to the sulfuric acid-hydrogen peroxide mixture at a rate that the temperature is controlled at about $10°$ C. or lower to form a second reaction mixture. The second reaction mixture is then held at a temperature in the range of from about $20°$ C. to about $50°$ C., preferably $25°$ C. to $30°$ C., for about 30 minutes to about 5 hours, preferably 1 to 2 hours to form a slurry containing a solid product of 2,5-dimethyl-2,5-dihydroxy hexane. The temperature of the slurry is then lowered to and maintained at about $10°$ C. or lower.

Preferably, water is added to the slurry controlled at about $10°$ C. or lower before separating the solid product from the aqueous solution. Optionally, the water-containing mixture can be further mixed by, for example, an agitation means to ensure a thorough washing of the solid product. The solid precipitate is the 2,5-dimethylhexane-2,5-dihydroperoxide which can be washed with solvents such as water or salt solutions. Washing is often desirable because it reduces the reaction rate between impurities and sulfated alkyl alcohol when the sulfated alkyl alcohol is added in the next step of the invention process.

Separation of unreacted reactants and impurities from the product can be conducted by any suitable means. For example, the unreacted reactants and impurities can be decanted, filtered, or centrifuged. The presently preferred separation means is decantation.

In the next step, a sulfated alkyl alcohol is added to the reaction containing the 2,5-dimethylhexane-2,5-dihydroperoxide. The term sulfated alkyl alcohol used in the present invention is referred to a mixture of sulfuric acid and an aliphatic alcohol which is formed by adding the alcohol to sulfuric acid. The presently preferred alcohol is an aliphatic alcohol having 1 to about 10 carbon atoms which can be a primary, secondary, or tertiary alcohol and can be linear, branched, or cyclic. The presently most preferred alcohol is t-butanol. The molar ratio of alcohol to sulfuric acid is in the range of from about 0.5 to about 5, preferably 0.8 to 1.5. The sulfated alkyl alcohol can be prepared by any mixing means and is preferably kept at a temperature below 25° C. The amount of the sulfated alkyl alcohol required to produce an alkyl derivative of 2,5-dimethylhexane-2,5-dihydroperoxide is generally dependent on the desired derivatives. For example, if one of the Rs is hydrogen, the molar ratio of the sulfated alkyl alcohol to 2,5-dimethylhexane-2,5-dihydroperoxide is about 0.5.

The 2,5-dimethylhexane-2,5-dihydroperoxide can also be dissolved in an alkyl alcohol before the addition of the sulfated alkyl alcohol to produce a different alkyl derivative of the 2,5-dimethylhexene-2,5-dihydroperoxide. The alkyl alcohol used is generally the same alcohol employed in the sulfated alkyl alcohol. The amount of alkyl alcohol used to dissolve the 2,5-dimethylhexane-2,5-dihydroperoxide is in the same range as described for the amount of alkyl alcohol used in the preparation of sulfated alkyl alcohol.

The alkyl derivatives of 2,5-dimethylhexane-2,5-dihydroperoxide can be separated and recovered by any conventional means such as, for example, phase separation.

The addition of the sulfated alkyl alcohol to 2,5-dimethylhexane-2,5-dihydroperoxide is generally carried out at 10° C. or lower. However, upon completion of the addition, the temperature of the reaction mixture is heated to a temperature in the range of from about 30° C. to about 60° C., preferably from 40° C. to 50° C., for about 1 to about 5 hours, preferably 2 to 3 hours to form a fourth reaction mixture. The third reaction mixture contains the desired derivative of the 2,5-dimethylhexane-2,5-dihydroperoxide and can also be mixed with any agitating means to ensure complete reaction.

EXAMPLES

Two 500 mL capacity open-top, jacketed reactors were used in the following examples. The reaction mixtures were stirred with a glass stir rod and a teflon stir paddle. Cooling was provided by a circulated glycol solution. The refrigerated unit used in these experiments was a Fisher Scientific Isotemp Refrigerated Circulating Bath Model 9500. It is capable of circulating 7 to 15 liter/min from a 10 liter reservoir. It has a temperature range of −35° C. to 150° C. Temperature was monitored by a K-type thermocouple in a thermowell which was placed in the reaction mixture. Materials were added to the reactor through the open top from a polypropylene separatory funnel. Samples were analyzed by HPLC using a Nova-pak C18 radial compression column (reverse-phase chromatrgraphy) with a mobile phase of methanol: water (90:10), and a refractive indices detector. Known standards were used to measure the products shown in the Tables below.

EXAMPLE I

This example illustrates the inventive process for preparing 2,5-dimethylhexane-2,5-dihydroperoxide using 70% hydrogen peroxide.

Hydrogen peroxide (quantity shown in Table I) was added to the open-top, jacketed reactor. The stirrer was started and the temperature was cooled to 5° C. Sulfuric acid (quantity shown in Table I) was then dripped (20 min.) into the reactor and the temperature of the mixture was controlled below 10° C. After addition of the sulfuric acid was completed, the temperature of the mixture was cooled back to 5° C. Solid 2,5-dimethyl-2,5-dihydroxy hexane (36.6 grams, 0.25 moles) was added to the mixture portionwise at a rate that the temperature was controlled below 10° C. (Note: at the outset solid 2,5-dimethyl-2,5-dihydroxy hexane dissolved in the $H_2O_2/H_2SO_4$ mixture; after a certain concentration was reached, a white solid precipitate fell out of solution with a temperature kick). At the end of the addition of the 2,5-dimethyl-2,5-dihydroxy hexane, the temperature of the reaction mixture was elevated to 25° C. and was held at 25° C. for one hour. At the completion of this holding period, the temperature was again lowered to 5° C. and 75 mL of water was added (10 min.) slowly to the mixture with the temperature controlled below 10° C. After 10 minutes of agitation the stirrer was stopped and the mixture was allowed to settle. The aqueous phase was carefully drained. Further washings were continued sequentially with one sodium sulfate/water (8.80 grams/75 mL) and two sodium bisulfate/water (17.58 grams/75 mL) washings. The washings were drained as described above for the aqueous phase. Afterwards the white solid 2,5-dimethylhexane-2,5-dihydroperoxide was collected via vacuum filtration upon a porcelain frit covered with filter paper and vacuum dried for hour. The results are shown in Table I.

TABLE I

| | 2,5-DIOOH[a] Preparation | | | | | | | | | | | |
|---|---|---|---|---|---|---|---|---|---|---|---|---|
| Run Number | $H_2O_2$ g | $H_2O_2$ Wt. % | $H_2O_2$ Moles | $H_2SO_4$ g | $H_2SO_4$ Wt. % | $H_2SO_4$ Moles | 2,5-DIOL[b] g | 2,5-DIOL Moles | Isolated Wt. Gms. | 2,5-DIOOH Wt. % | 2,5-DIOOH Wt. Gms. | Yield % |
| 1 | 115.58 | 50 | 1.70 | 107.00 | 78 | 0.85 | 25.00 | 0.171 | 24.40 | 74.8 | 18.24 | 59.8 |
| 2 | 115.58 | 50 | 1.70 | 107.00 | 78 | 0.85 | 25.00 | 0.171 | 29.38 | 62.5 | 18.37 | 60.3 |
| 3 | 82.58 | 70 | 1.70 | 107.00 | 78 | 0.85 | 25.00 | 0.171 | 29.23 | 79.4 | 28.22 | 76.2 |
| 4 | 66.00 | 70 | 1.36 | 85.60 | 78 | 0.68 | 25.00 | 0.171 | 29.60 | 79.7 | 23.60 | 77.5 |
| 5 | 121.40 | 70 | 2.50 | 157.50 | 78 | 1.25 | 36.60 | 0.250 | 48.09 | 71.9 | 34.58 | 77.5 |
| 6 | 121.40 | 70 | 1.70 | 157.50 | 78 | 1.25 | 36.60 | 0.251 | 48.40 | 74.2 | 35.92 | 80.5 |
| 7 | 121.40 | 70 | 1.70 | 157.50 | 78 | 1.25 | 36.60 | 0.251 | 55.14 | 63.2 | 34.87 | 78.1 |
| 8 | 121.40 | 70 | 1.70 | 157.50 | 78 | 1.25 | 36.60 | 0.251 | 48.51 | 71.2 | 34.52 | 77.4 |

TABLE I-continued

| | 2,5-DIOOH$^a$ Preparation | | | | | | | | | | | |
|---|---|---|---|---|---|---|---|---|---|---|---|---|
| Run Number | H$_2$O$_2$ g | H$_2$O$_2$ Wt. % | H$_2$O$_2$ Moles | H$_2$SO$_4$ g | H$_2$SO$_4$ Wt. % | H$_2$SO$_4$ Moles | 2,5-DIOL$^b$ g | 2,5-DIOL Moles | Isolated Wt. Gms. | 2,5-DIOOH Wt. % | 2,5-DIOOH Wt. Gms. | Yield % |
| 9 | 170.00 | 50 | 2.50 | 157.50 | 78 | 1.25 | 36.60 | 0.251 | 36.04 | 71.8 | 25.86 | 58.0 |
| 101 | 141.60 | 60 | 2.50 | 157.50 | 78 | 1.25 | 36.60 | 0.251 | 42.28 | 82.1 | 34.72 | 77.8 |
| 102 | 141.60 | 60 | 2.40 | 157.50 | 78 | 1.25 | 36.60 | 0.251 | 44.45 | 77.5 | 34.43 | 77.2 |
| 103 | 141.60 | 60 | 2.50 | 157.50 | 78 | 1.25 | 36.60 | 0.251 | 45.74 | 76.9 | 35.15 | 78.8 |
| 104 | 121.40 | 70 | 2.50 | 157.50 | 78 | 1.25 | 36.60 | 0.251 | 54.17 | 64.6 | 34.97 | 78.4 |
| 106 | 121.40 | 70 | 2.50 | 157.50 | 78 | 1.25 | 36.60 | 0.251 | 54.90 | 65.3 | 35.85 | 80.3 |
| 107 | 121.40 | 70 | 2.50 | 157.50 | 78 | 1.25 | 36.60 | 0.251 | 41.49 | 82.5 | 34.23 | 76.7 |

$^a$2,5-DIOOH denotes 2.5-dimethylhexane-2,5-dihydroperoxide.
$^b$2,5-DIOL denotes 2,5-dimethyl-2,5-dihydroperoxy hexane.

As shown in Table I, when 70% hydrogen peroxide was used (runs 3-8 and 104-107) the yield of 2,5-dimethylhexane-2,5-dihydroperoxide was consistently substantially higher than that when 50% (runs 1-2 and 9) hydrogen peroxide was used. Similarly, when 60% hydrogen peroxide was used (runs 101-103), the yield of 2,5-dimethylhexane-2,5-dihydroperoxide was also substantially higher than that when 50% hydrogen peroxide was used. All comparative runs, runs 1-2 (50% H$_2$O$_2$) and runs 6-8 (70% hydrogen peroxide) as well as run 9 (50% hydrogen peroxide), runs 101-103 (60% hydrogen peroxide), and runs 5 and 104-107 (70% hydrogen peroxide), were carried out under the same condition and the same reagent molarities. It is concluded that, on the average, the yield of 2,5-dimethylhexane-2,5-dihydroperoxide was increased by at least 31% by using either 60% or 70% H$_2$O$_2$ over 50% H$_2$O$_2$ as reagent.

EXAMPLE II

This example illustrate the inventive one-step synthesis of a derivative of 2,5-dimethylhexane-2,5-dihydroperoxide.

The first stage of the runs were identical to those described in Example I except that at the end of the washing steps, t-butanol (88 wt %, 71.5 grams, 0.85 mole) was added to the wet, white 2,5-dimethylhexane-2,5-dihydroperoxide solid was left in the reactor and the temperature was elevated to 32° C. After all of the solid 2,5-DIOOH was dissolved, a two-layer solution was obtained and the bottom layer was carefully drained from the reactor. While making the 2,5-dimethylhexane-2,5-dihydroperoxide intermediate in the open-top reactor, t-butanol (88 wt %, 71.5 grams, 0.85 moles) was added (20 min.) dropwise into a stirred solution of sulfuric acid (78 wt %, 104.7 grams, 0.83 moles) in a 200 mL glass beaker immersed in a 5° C. ice bath. (Note: the temperature of this sulfated t-butanol preparation was kept below 20° C.) This pre-mixed t-butanol/sulfuric acid (sulfated t-butanol) solution was then added to the t-butanol solution of 2,5-dimethylhexane-2,5-dihydroperoxide at 25° C. Very quickly a white solid precipitate fell out of the solution and the temperature of this white slurry was heated up to 40° C. Gradually, all of the solid went back into solution and the solution was held at 40° C. for up to four hours. Afterwards, the bottom layer of this two-layer mixture was carefully drained from the reactor and the top product layer was washed with 112 mL of water and later with sodium carbonate/water (7.5 grams/75 mL) solution. The results are shown in Table II.

TABLE II

| | | | | | 2,5-DI$^a$ Preparation$^b$ | | | | | | | |
|---|---|---|---|---|---|---|---|---|---|---|---|---|
| Run | TBA$^c$ gM. | TBA Mole | TBA/H$_2$SO$_4$ gM. | TBA/H$_2$SO$_4$ Mole | Product Wt. Gms. | Cyclic$^d$ Wt. % | Cyclic Wt. Gms. | 2,5-DI Wt. % | 2,5-DI Wt. Gms. | Yield % | DITBP$^e$ Wt. % | DITBP Wt. Gms. |
| 10 | 71.5 | 0.85 | 71.5/104.7 | 0.85/0.83 | 56.18 | 1.94 | 1.08 | 91.6 | 51.45 | 70.8 | 3.30 | 1.85 |
| 11 | 71.5 | 0.85 | 71.5/104.7 | 0.85/0.83 | 56.97 | 2.04 | 1.16 | 91.9 | 52.38 | 72.1 | 3.40 | 1.93 |
| 12 | 71.5 | 0.85 | 71.5/104.7 | 0.85/0.83 | 54.96 | 2.59 | 1.42 | 88.4 | 48.59 | 66.8 | 2.41 | 1.32 |
| 13 | 71.5 | 0.85 | 0/104.7 | 0/0.83 | 53.71 | 6.81 | 3.66 | 82.7 | 44.43 | 61.1 | 5.92 | 3.17 |
| 14 | 71.5 | 0.85 | 0/104.7 | 0/0.83 | 50.18 | 5.26 | 2.64 | 90.1 | 45.21 | 62.2 | 2.79 | 1.39 |
| 15 | 81.7 | 0.97 | 0/119.7 | 0/0.95 | 50.43 | 5.69 | 2.86 | 88.8 | 44.79 | 61.6 | 3.44 | 1.73 |
| 16 | 71.5 | 0.85 | 0/104.7 | 0/0.83 | 50.92 | 5.75 | 2.93 | 90.1 | 45.89 | 63.1 | 3.27 | 1.66 |
| 17 | 81.7 | 0.97 | 0/119.7 | 0/0.95 | 50.70 | 5.93 | 3.00 | 88.0 | 44.60 | 61.4 | 3.85 | 1.95 |
| 18 | 71.5 | 0.85 | 0/104.7 | 0/0.83 | 51.55 | 6.93 | 3.57 | 84.5 | 43.57 | 59.9 | 4.16 | 2.14 |
| 19 | 71.5 | 0.85 | 81.7/119.7 | 0.97/0.95 | 59.63 | 1.79 | 1.07 | 85.2 | 50.82 | 69.9 | 3.77 | 2.25 |
| 20 | 71.5 | 0.85 | 81.7/119.7 | 0.97/0.95 | 61.33 | 2.98 | 1.82 | 80.7 | 49.48 | 68.1 | 5.80 | 3.55 |
| 21 | 81.7 | 0.97 | 0/119.7 | 0/0.95 | 54.07 | 6.68 | 3.61 | 83.6 | 45.20 | 62.2 | 6.59 | 3.56 |
| 22 | 71.5 | 0.85 | 0/104.7 | 0/0.83 | 51.90 | 5.37 | 2.78 | 88.7 | 46.04 | 63.3 | 3.18 | 1.65 |
| 23 | 71.5 | 0.85 | 0/104.7 | 0/0.83 | 52.35 | 5.55 | 2.90 | 87.2 | 45.64 | 62.8 | 3.41 | 1.78 |
| 24 | 71.5 | 0.85 | 0/104.7 | 0/0.83 | 50.06 | 3.69 | 1.84 | 92.1 | 46.11 | 63.4 | 2.63 | 1.31 |
| 25 | 71.5 | 0.85 | 71.5/104.7 | 0.85/0.83 | 57.93 | 1.80 | 1.04 | 87.3 | 50.55 | 69.5 | 3.65 | 2.12 |
| 26 | 81.7 | 0.97 | 71.5/104.7 | 0.85/0.83 | 56.15 | 1.86 | 1.04 | 86.1 | 48.35 | 66.5 | 2.86 | 1.60 |
| 27 | 71.5 | 0.85 | 0/104.7 | 0/0.83 | 51.63 | 4.86 | 2.50 | 89.5 | 46.20 | 63.6 | 3.42 | 1.76 |
| 28 | 71.5 | 0.85 | 0/104.7 | 0/0.83 | 47.96 | 3.51 | 1.68 | 91.3 | 43.77 | 60.2 | 2.81 | 1.34 |
| 29 | 71.5 | 0.85 | 71.5/104.7 | 0.85/0.83 | 55.65 | 1.74 | 0.97 | 88.4 | 49.18 | 67.7 | 3.02 | 1.67 |
| 30 | 71.5 | 0.85 | 71.5/104.7 | 0.85/0.83 | 55.25 | 1.79 | 0.98 | 90.5 | 50.01 | 68.8 | 2.70 | 1.49 |
| 31 | 71.5 | 0.85 | 0/104.7 | 0/0.83 | 52.22 | 4.95 | 2.58 | 88.3 | 46.09 | 63.4 | 3.28 | 1.71 |
| 32 | 71.5 | 0.85 | 0/104.7 | 0/0.83 | 53.49 | 6.00 | 3.20 | 88.5 | 47.34 | 65.1 | 3.41 | 1.82 |
| 33 | 60.0 | 0.71 | 35.75/104.7 | 0.43/0.83 | 60.15 | 5.07 | 3.05 | 75.4 | 45.38 | 62.4 | 3.89 | 2.33 |
| 34 | 71.5 | 0.85 | 0/104.7 | 0/0.83 | 52.59 | 4.50 | 2.36 | 87.3 | 45.91 | 63.2 | 3.54 | 1.86 |
| 35 | 71.5 | 0.85 | 0/104.7 | 0/0.83 | 52.87 | 5.76 | 3.04 | 86.2 | 45.56 | 62.7 | 3.52 | 1.86 |
| 36 | 71.5 | 0.85 | 71.5/104.7 | 0.85/0.83 | 58.46 | 2.00 | 1.16 | 83.1 | 48.54 | 66.8 | 3.58 | 2.09 |
| 37 | 71.5 | 0.85 | 71.5/104.7 | 0.85/0.83 | 58.93 | 2.80 | 1.64 | 81.3 | 47.89 | 65.9 | 3.11 | 1.83 |
| 38 | 71.5 | 0.85 | 0/104.7 | 0/0.83 | 51.49 | 4.62 | 2.38 | 88.3 | 45.48 | 62.6 | 3.56 | 1.83 |

TABLE II-continued

| | | | | | 2,5-DI[a] Preparation[b] | | | | | | | |
|---|---|---|---|---|---|---|---|---|---|---|---|---|
| Run | TBA[c] gM. | TBA Mole | TBA/H$_2$SO$_4$ gM. | TBA/H$_2$SO$_4$ Mole | Product Wt. Gms. | Cyclic[d] Wt. % | Cyclic Wt. Gms. | 2,5-DI Wt. % | 2,5-DI Wt. Gms. | Yield % | DITBP[e] Wt. % | DITBP Wt. Gms. |
| 39 | 71.5 | 0.85 | 0/104.7 | 0/0.83 | 53.43 | 5.42 | 2.89 | 88.9 | 47.51 | 65.4 | 3.76 | 2.00 |
| 40 | 81.7 | 0.97 | 0/119.7 | 0/0.95 | 53.73 | 5.21 | 2.80 | 88.2 | 47.39 | 65.2 | 5.57 | 2.99 |
| 41 | 71.5 | 0.85 | 71.5/104.7 | 0.85/0.83 | 56.62 | 2.47 | 1.39 | 85.4 | 48.34 | 66.5 | 3.44 | 1.95 |
| 42 | 71.5 | 0.85 | 71.5/104.7 | 0.85/0.83 | 58.50 | 3.31 | 1.93 | 80.1 | 46.83 | 64.4 | 3.49 | 2.04 |
| 43 | 71.5 | 0.85 | 71.5/104.7 | 0.85/0.83 | 54.43 | 2.27 | 1.23 | 89.8 | 48.87 | 67.2 | 2.22 | 1.21 |
| 44 | 65.0 | 0.77 | 71.5/96.1 | 0.85/0.83 | 68.14 | 3.11 | 2.12 | 72.9 | 49.67 | 68.3 | 4.72 | 3.21 |
| 45 | 71.5 | 0.85 | 71.5/104.7 | 0.85/0.83 | 56.42 | 2.16 | 1.21 | 86.7 | 48.90 | 67.3 | 4.70 | 2.65 |
| 46 | 60.0 | 0.71 | 81.7/119.7 | 0.97/0.95 | 63.11 | 2.39 | 1.50 | 79.5 | 50.15 | 69.0 | 4.43 | 2.79 |
| 47 | 71.5 | 0.85 | 71.5/104.7 | 0.85/0.83 | 54.62 | 2.20 | 1.20 | 92.5 | 50.51 | 69.5 | 3.68 | 2.00 |
| 48 | 71.5 | 0.85 | 71.5/104.7 | 0.85/0.83 | 53.93 | 2.21 | 1.192 | 92.0 | 50.18 | 69.0 | 3.46 | 1.86 |
| 49 | 71.5 | 0.85 | 71.5/104.7 | 0.85/0.83 | 56.94 | 2.42 | 1.37 | 88.4 | 50.35 | 69.3 | 3.21 | 1.82 |
| 50 | 60.0 | 0.71 | 81.7/119.7 | 0.97/0.95 | 54.63 | 2.45 | 1.34 | 93.5 | 51.07 | 70.2 | 3.37 | 1.84 |
| 51 | 71.5 | 0.85 | 81.7/119.7 | 0.97/0.95 | 54.21 | 1.81 | 0.98 | 93.5 | 50.69 | 69.7 | 3.91 | 2.12 |
| 52 | 71.5 | 0.85 | 71.5/96.1 | 0.85/0.83 | 58.81 | 3.01 | 1.76 | 86.6 | 50.91 | 70.0 | 3.60 | 2.12 |
| 53 | 143.0 | 1.70 | 0/104.7 | 0/0.83 | 52.27 | 1.99 | 1.04 | 84.3 | 44.08 | 60.6 | 2.86 | 1.49 |
| 54 | 71.5 | 0.85 | 71.5/104.7 | 0.85/0.83 | 52.38 | 2.39 | 1.25 | 83.1 | 43.55 | 59.9 | 4.36 | 2.28 |
| 55 | 71.5 | 0.85 | 71.5/104.7 | 0.85/0.83 | 53.88 | 2.67 | 1.43 | 93.6 | 50.41 | 69.3 | 3.05 | 1.64 |
| 56 | 71.5 | 0.85 | 71.5/104.7 | 0.85/0.83 | 55.29 | 3.32 | 1.83 | 90.2 | 49.89 | 68.6 | 4.20 | 2.32 |
| 57 | 71.5 | 0.85 | 71.5/104.7 | 0.85/0.83 | 55.33 | 3.39 | 1.87 | 89.2 | 49.36 | 67.9 | 5.1 | 2.85 |
| 58 | 60.0 | 0.71 | 42.9/62.8 | 0.51/0.50 | 51.97 | 3.54 | 1.84 | 67.7 | 35.16 | 48.4 | 2.60 | 1.35 |
| 59 | 60.0 | 0.71 | 50.1/73.3 | 0.60/0.58 | 55.30 | 4.58 | 2.53 | 80.8 | 44.67 | 61.4 | 4.29 | 2.37 |
| 60 | 71.5 | 0.85 | 57.2/83.7 | 0.68/0.66 | 54.19 | 3.58 | 1.93 | 89.3 | 48.41 | 66.6 | 3.15 | 2.70 |
| 61 | 71.5 | 0.85 | 71.5/104.7 | 0.85/0.83 | 57.89 | 4.99 | 2.88 | 87.2 | 50.46 | 69.4 | 5.26 | 3.04 |
| 62 | 71.5 | 0.85 | 71.5/104.7 | 0.85/0.83 | 56.11 | 3.36 | 1.88 | 91.1 | 51.14 | 70.3 | 3.69 | 2.07 |
| 63 | 71.5 | 0.85 | 71.5/104.7 | 0.85/0.83 | 57.05 | 4.04 | 2.30 | 89.6 | 51.09 | 70.3 | 5.25 | 2.99 |

[a]2,5-DI denote 2,5-dimethyl-2,5-di(t-butylperoxy)hexane.
[b]All runs were carried out under ambient pressure and at 40° C. for 2 hours, except runs 55–60.
[c]TBA, t-butanol.
[d]Cyclic denotes by-product, 3,3,6,6-tetramethyl-1,2-dioxacyclohexane.
[e]DITBP, di-t-butylperoxide, a by-product.

Table II shows that in the absence of a pre-mixed "sulfated butanol (for example, comparing runs 13–14, 16, 18, 22–24, 27–28, 31–32, 34–35, 38–39, and 53 with runs 10–12, 25–26, 29–30, 36–37, 41–45, 47–49, 52, and 54) the yield of 2,5-dimethyl-2,5di(t-butylperoxy)hexane was consistently, substantially higher in the presence of pre-mixed "sulfated t-butanol" than that in the absence of the "sulfated butanol". Higher holding temperatures (runs 55–57 and 62–63) did not improve the yield. However, lowering the amount of t-butanol (run 33) or both t-butanol and sulfuric acid (runs 58–59) in the sulfated t-butanol adversely affected the yield of 2,5-dimethyl-2,5-di(t-butylperoxy)hexane.

Table II further shows that the amount of 3,3,6,6-tetramethyl-1,2-dioxacyclohexane was greatly reduced by addition of pre-mixed "sulfated t-butanol" by as much as 75% (runs 18 and 29).

EXAMPLE III

This example shows that a mono-derivative of 2,5-dimethylhexane-2,5-dihydroperoxide such as 2,5-dimethyl-t-butylperoxyhexane can be prepared by the inventive one step process.

The runs were carried out the same as those described in Example II with the exception that 2,5-dimethylhexane-2,5-dihydroperoxide was directly dissolved in the pre-mixed sulfated t-butanol instead of in t-butanol followed by the addition of the sulfated t-butanol. The results are shown in Table III.

For comparison, run 70 was carried out by isolating the peroxide, 2,5-dimethylhexane-2,5-dihydroperoxide, from the reactor followed by washing and placing it back to the reactor. Sulfated t-butanol was then added to the peroxide.

TABLE III

| | | | 2,5-MONO[a] Preparation | | | | | | |
|---|---|---|---|---|---|---|---|---|---|
| Run | TBA[b]/H$_2$SO$_4$ gM. | TBA/H$_2$SO$_4$ Mole | Holding Time Hr. | Product Wt. Gms. | 2,5-MONO Wt. % | 2,5-MONO Wt. Gms. | Yield % | 2,5-DI[c] Wt. % | 2,5-DI Wt. Gms. |
| 65[d] | 71.5/104.7 | 0.85/0.83 | 2.17 | 44.64 | 84.7 | 37.80 | 64.4 | 2.07 | 0.92 |
| 66 | 71.5/104.7 | 0.85/0.83 | 2.00 | 45.27 | 80.8 | 36.58 | 62.4 | 2.25 | 1.02 |
| 67[d] | 71.5/104.7 | 0.85/0.83 | 1.33 | 47.35 | 78.2 | 37.01 | 63.1 | 2.52 | 1.19 |
| 68 | 71.5/104.7 | 0.85/0.83 | 2.33 | 46.18 | 85.6 | 39.53 | 67.4 | 1.97 | 0.91 |
| 69[e] | 71.5/104.7 | 0.85/0.83 | 2.42 | 48.18 | 79.1 | 38.11 | 65.0 | 1.59 | 0.77 |
| 70[e,f] | 71.5/104.7 | 0.85/0.83 | 2.00 | 51.05 | 0 | 0 | — | 92.90 | 47.43 |

[a]2,5-MONO denotes 2,5-dimethyl-2-t-butylperoxyhexane.
[b]See footnote c, Table II.
[c]See footnote a, Table II.
[d]Product was washed with H$_2$O/NaHSO$_4$.
[e]Product was washed with a mixture of H$_2$O/Na$_2$CO$_3$/NaHSO$_4$.
[f]Run 70 was carried out by the same procedure except that TBA/H$_2$SO$_4$ was added to the peroxide that had been isolated from the reactor, washed and then placed back to the reactor. No 2,5-MONO was obtained. The cyclic compound was 2.70 wt %, DITBP (see Table II, footnote e) made up the rest of the product mixture.

The results in Table III shows that addition of the same amount of sulfated t-butanol as described in Example II without dissolving the 2,5-dimethylhexane-2,5-dihydroperoxide in t-butanol, the major derivative synthesized was 2,5-dimethyl-2-t-butylperoxyhexane. Increasing reaction time to over 2 hours did not increase the yield of 2,5-dimethyl-2,5-di(t-butylperoxy)hexane.

Table III further shows that, if the peroxide is isolated from the reactor as disclosed in U.S. Pat. No. 3,117,166, no mono-derivative of the peroxide was made. Instead, 2,5-dimethyl-2,5-di(t-butylperoxy)hexane was synthesized (run 70).

EXAMPLE IV

This example illustrates that isolating the 2,5-dimethylhexane-2,5-dihydroperoxide followed by dissolving the peroxide in t-butanol and reacting with sulfated t-butanol did not produce mono-derivative of the peroxide.

The runs were carried out the same as those described in Example II except that the 2,5-dimethylhexane-2,5-dihydroperoxide produced was isolated from the reactor and washed followed by placing it back to the reactor. The results are shown in Table IV. As can be seen, no mono-derivative of 2,5-dimethylhexane-2,5-dihydroperoxide can be made by this process.

The results shown in the above examples clearly demonstrate that the present invention is well adapted to carry out the objects and attain the ends and advantages mentioned as well as those inherent therein. While modifications may be made by those skilled in the art, such modifications are encompassed with the spirit of the present invention as defined by the specification and the claims.

TABLE IV

| | | | | | 2,5-DI$^a$ Preparation$^b$ | | | | | | | |
|---|---|---|---|---|---|---|---|---|---|---|---|---|
| Run | TBA$^c$ gM. | TBA Mole | TBA/H$_2$SO$_4$ gM. | TBA/H$_2$SO$_4$ Mole | Product Wt. Gms. | Cyclic$^d$ Wt. % | Cyclic Wt. Gms. | 2,5-DI Wt. % | 2,5-DI Wt. Gms. | Yield % | DITBP$^e$ Wt. % | DITBP Wt. Gms. |
| 71 | 71.5 | 0.85 | 71.5/104.7 | 0.85/0.83 | 57.09 | 1.36 | 0.77 | 87.5 | 49.98 | 68.8 | 5.60 | 3.20 |
| 72 | 71.5 | 0.85 | 71.5/104.7 | 0.85/0.83 | 57.16 | 0.91 | 0.52 | 88.7 | 50.72 | 69.8 | 6.14 | 3.51 |

$a, b, c, d, e$ See corresponding footnotes in Table II.

That which is claimed is:

1. A one-step process for producing 2,5-dimethylhexane-2,5-dihydroperoxide and alkyl derivative thereof comprising:
   (a) adding sulfuric acid to an at least 60% hydrogen peroxide solution to form a first reaction mixture wherein said first reaction mixture is controlled at a temperature in the range of from about −10° C. to about 10° C.;
   (b) adding 2,5-dimethyl-2,5-dihydroxy hexane to said first reaction mixture to form a second reaction mixture wherein said second reaction mixture is maintained at a temperature in the range of from about 20° C. to about 50° C. for about 5 minutes to about 5 hours whereby a slurry is formed, wherein said slurry contains the solid product of 2,5-dimethylhexane-2,5-dihydroperoxide;
   (c) lowering the temperature of said slurry to the range of from about −10° C. to about 10° C.; thereafter
   (d) removing unreacted reactants and impurities from said solid product; and
   (e) adding sulfated alkyl alcohol to said solid product to form a third reaction mixture wherein said sulfated alkyl alcohol is prepared by mixing said alkyl alcohol with sulfuric acid and said third reaction mixture is maintained at a temperature in the range of from about 30° C. to about 60° C. for about 1 to about 5 hours to prepare said alkyl derivative.

2. A process according to claim 1 wherein said alkyl derivative is recovered from the resulting reaction mixture formed in step (e).

3. A process according to claim 1 wherein said solid product formed in step (b) is dissolved, after completion of step (d), in said alkyl alcohol of step (e) prior to adding said sulfated alkyl alcohol to said solid product.

4. A process according to claim 1 wherein said alkyl derivative has the formula of CH$_3$(CH$_3$)C(O$_2$R)CH$_2$CH$_2$(O$_2$R)(CH$_3$)CH$_3$.

5. A process according to claim 4 wherein R is a C$_1$–C$_{10}$ alkyl selected from linear alkyls, cyclic alkyls and branched alkyls.

6. A process according to claim 1 wherein said alkyl alcohol is t-butanol.

7. A process according to claim 1 wherein said alkyl derivative is 2,5-dimethyl-2-t-butylperoxyhexane.

8. A process according to claim 1 wherein said alkyl derivative is 2,5-dimethyl-2,5-di(t-butylperoxy)hexane.

9. A process for preparing 2,5-dimethyl-2-t-butylperoxyhexane comprising:
   (a) adding sulfuric acid to a 60–70% hydrogen peroxide solution to form a first reaction mixture wherein said first reaction mixture is controlled at a temperature in the range of from about −10° C. to about 10° C.;
   (b) adding 2,5-dimethyl-2,5-dihydroxy hexane to said first reaction mixture to form a second reaction mixture wherein said second reaction mixture is maintained at a temperature in the range of from about 20° C. to about 50° C. for about 30 minutes to about 5 hours whereby a slurry is formed, wherein said slurry contains a solid product of 2,5-dimethylhexane-2,5-dihydroperoxide;
   (c) lowering the temperature of said slurry to the range of from about −10° C. to about 10° C.; thereafter
   (d) adding water to said slurry and washing said solid product; and
   (e) adding sulfated t-butanol to said solid product to form a third reaction mixture; wherein said sulfated t-butanol is prepared by mixing t-butanol with sulfuric acid and said third reaction mixture is maintained at a temperature in the range of from about 30° C. to about 60° C. for about 1 to about 5 hours to prepare said 2,5-dimethyl-2-t-butylperoxyhexane.

10. A process for preparing 1,5-dimethyl-2-5-di(t-butylperoxy)hexane comprising:
   (a) adding sulfuric acid to a 60–70% hydrogen peroxide solution to form a first reaction mixture wherein said first reaction mixture is controlled at a temperature in the range of from about −10° C. to about 10° C.;
   (b) adding 2,5-dimethyl-2,5-dihydroxy hexane to said first reaction mixture to form a second reaction mixture wherein said second reaction mixture is maintained at a temperature in the range of from about 20° C. to about 50° C. for about 30 minutes to about 5 hours whereby a slurry is formed, wherein said slurry contains a solid product of 2,5-dimethylhexane-2,5-dihydroperoxide;

(c) lowering the temperature of said slurry to the range of from about −10° C. to about 10° C.; thereafter
(d) adding water to said slurry and washing said solid product;
(e) adding t-butanol to said solid product to form an intermediate solution; and
(f) adding sulfated t-butanol to said intermediate solution to form a third reaction mixture; wherein said sulfated t-butanol is prepared by mixing t-butanol with sulfuric acid and said third reaction mixture is maintained at a temperature in the range of from about 30° C. to about 60° C. for about 1 to about 5 hours to prepare said 2,5-dimethyl-2,5-di(t-butylperoxy)hexane.

* * * * *